United States Patent [19]
Gordon

[11] Patent Number: 5,429,728
[45] Date of Patent: Jul. 4, 1995

[54] ELECTROOSMOTIC FLOW CONTROL USING BACK PRESSURE IN CAPILLARY ELECTROPHORESIS

[75] Inventor: Gary B. Gordon, Saratoga, Calif.
[73] Assignee: Hewlett-Packard Company, Palo Alto, Calif.
[21] Appl. No.: 125,878
[22] Filed: Sep. 23, 1993

Related U.S. Application Data

[63] Continuation-in-part of Ser. No. 938,665, Aug. 31, 1992, Pat. No. 5,324,413.
[51] Int. Cl.$^6$ .................... G01N 27/26; G01N 27/447
[52] U.S. Cl. ............................. 204/180.1; 204/299 R
[58] Field of Search .............. 204/299 R, 180.1, 183.3

[56] References Cited

U.S. PATENT DOCUMENTS

| | | | |
|---|---|---|---|
| 3,705,845 | 12/1972 | Everaerts | 204/183.3 |
| 3,869,365 | 3/1975 | Sunden | 204/183.3 |

OTHER PUBLICATIONS

Wim Th. Kok "Off-Column Detection with Pressure Compensation in Capilly Electrophoresis" Analytical Chemistry, vol. 65, No. 14 (Jul. 1993) 1853-1860.

Douglass McManigill et al "Dispersion in capillary electrophoresis with external flow control methods" Journal of Chromatography A vol. 652 No. 1 (Oct. 1993) 283-289.

U. R. Tjaden et al "Automated isotachophoretic analyte focusing for capillary zone electrophoresis in a single capillary using hydrodynamic back-pressure programming" Journal of Chromatography (Jul. 1993) 155-162.

Ranjit R. Deshmukh & Milan Bier "Counterflow in isotachophoresis: Computer simulation and experimental studies" Electrophoresis vol. 14 No. 3 (Mar. 1993) 205-213.

F. M. Everaerts, "Isotachophoretic Experiments with Counter Flow of Electrolyte" Journal of Chromatography 123 no month available (1976) 139-148.

Electrokinetic Dispersion in Capillary Electrophoresis, Ravindra Datta and Veerabhadra Kotamarthi, AIChE Journal, vol. 36, No. 6, pp. 916-923, Jun. 1990.

Isotachophoretic Experiments with a Counter Flow Electrolyte, F. M. Everarts, Th. P. E. M. Verheggen, and J. L. M. Van De Veene, 123 Journal of Chromatography, pp. 139-148, no month available 1976.

*Primary Examiner*—Kathryn Gorgos
*Assistant Examiner*—John S. Starsiak, Jr.

[57] ABSTRACT

A separation capillary in a capillary electrophoresis apparatus is less than 20 microns high to restrict the flow velocity profile of the EOF to being substantially parabolic. The capillary is preferably rectangular with an aspect ratio of at least 2:1, and preferably at least 10:1, in order to increase bulk flow. Hydrostatic back pressure is applied to the capillary to reduce or cancel the EOF. The back pressure is preferably at least 50% as strong as the forward-directed EOF in order to reduce EOF, and thereby to increase resoulution.

4 Claims, 3 Drawing Sheets

ELECTROOSMOTIC FLOW

COMPOSITE FLOW

HYDROSTATIC FLOW

ELECTROOSMOTIC FLOW CONTROL USING BACK PRESSURE IN CAPILLARY ELECTROPHORESIS

CROSS-REFERENCE TO RELATED APPLICATIONS

This is a continuation-in-part of U.S. patent application Ser. No. 07/938,665, now U.S. Pat. No. 5,324,413 filed 31 Aug. 1992, with the same inventor.

BACKGROUND OF THE INVENTION

1. Field of the Invention

This invention relates to a capillary structure and a method for controlling electroosmotic flow (EOF) in a capillary electrophoresis apparatus.

2. Description of the Related Art

Capillary electrophoresis (CE) is a well-known analytical technique in which the components (ionic species) of an analyte are separated based on their ratio of charge to mobility. In a typical capillary zone electrophoresis (CZE) system (a common implementation of CE), the analyte is introduced along with a carrier electrolyte or buffer into one end of a small-bore capillary and a strong electrical separation potential (an electric field) is applied axially over the length of the capillary. More highly charged and more mobile components of the analyte then tend to move faster through the capillary, so that components are separated into different bands or regions. A detector, which is usually light-based, is then used to sense the passage of each band past a detection region and to determine the speed of migration of the various bands (also known as "peaks") through the capillary. The absolute and relative speeds of migration, as well as spectrographic or other detector information, can then be compared with known patterns to determine in part which chemical or biochemical components are in the analyte.

Ideally, the various components or species in the analyte separate into narrow, well-separated bands: if adjacent bands are too broad, they may overlap and make it impossible even to distinguish them.

Capillary electrophoresis is most often performed in circular capillaries fifty microns in inside diameter, as this size has been found empirically to give favorable performance tradeoffs. This size is large enough to allow sensitive detection, yet not so large as to produce excessive radial heating and viscosity gradients which broaden bands and destroy resolution.

At this fifty-micron capillary diameter, electroosmotic flow (EOF) produces a well-developed plug-shaped flow. At the edge of the capillary, flow is laminar and in sheer, but the thickness of this double-layer region is on the order of microns with commonly used buffers and pH's. The flow velocity profile therefore rises rapidly at the outer microns of the flow plug, and then transitions to a fairly flat region across the wide center of the flow profile. Thus, most of the electrolyte flows at the same velocity, and undesirable laminar mixing, which would broaden the peaks, is minimized. The penalty for this operating regime is, however, substantial EOF, which is discussed in greater detail below.

Capillary tubes used in CE are normally made of fused silica. Above about pH 4, negative ions in the carrier electrolyte attach to silanol groups of the fused silica and leave a concentration of positively charged ions near the radially inner side of the double layer. The resulting layer of negative ions attached to the silica surface and the layer of positive ions extending away from the surface form the well-known "double layer" structure near the inner capillary wall. Under the influence of the large electric field applied axially along the capillary, this positive ionic charge concentration results in considerable undesirable pumping forward towards the cathode, that is, toward the end of the capillary that is at the "negative" region of the applied electric field. Electroosmotic flow (EOF) is the bulk flow in the separation capillary that is caused by this pumping, that is, that results from the ions within the double layer being propelled by the axial separation potential. This potential also carries along the neutrally charged inner region of buffer in the capillary.

A significant problem associated with EOF is that it may cause the analyte to move through the capillary so fast that the components of the analyte do not have time to separate clearly enough to distinguish and identify them. Although some EOF may be desirable so as to allow species of both positive and negative ionic charge to reach the detector, there has consequently been a long-standing and frequently articulated need to reduce or control EOF.

One way to offset the effect of EOF is simply to make the capillary longer so that the components of the analyte will have farther to travel and therefore more time in which to be separated, provided, however, that the potential along the capillary is increased proportionately. On the other hand, one typically wishes to make the capillary shorter in order to permit the use of more affordable power supplies: the longer the capillary is, the stronger the separation potential must be in order to achieve the same potential gradient or field.

Other conventional attempts to control EOF have been only partially successful, or successful only under a narrow range of conditions. One known method involves limiting separations to only those with low buffer pH, which limits the usefulness of the CE device. Another method involves greatly increasing the buffer concentration; however, this increases Joule heating, which worsens CE resolution. Yet another method involves increasing buffer viscosity, but this may alter the selectivity of the device. Still another method involves chemically bonding some compound to the capillary wall to terminate the silanol sites, but such coatings do not remain stable.

According to another category of methods for controlling EOF, at least one radial electric field is applied to the capillary by coaxial conductors or resistors. Such fields include tracking fields and sheath fields of constant potential. Experience has shown, however, that neither of these configurations is effective over a wide pH range.

The superposition of laminar flow upon EOF is discussed in the article "Electrokinetic Dispersion in Capillary Electrophoresis," Ravindra Datta and Veerabhadra Kotamarthi, AIChE Journal, Vol. 36, No. 6, June 1990. In this article it is shown that radial viscosity changes from Joule heating produce a slightly convex "plug" flow profile, which can be flattened by application of a mild back pressure. By setting the back pressure properly, lower dispersion was realized and plate height minimized, that is, the separation bands were narrowed.

It is conventionally believed that strong back pressure reduces the sharpness of zone boundaries, that is, that it causes band-broadening. The assumed reason is that the back pressure causes a counterflow or eddy-currents along the capillary: electroosmotic forces act primarily at the outer edges of the plug and propel that region towards the detector whereas hydrostatic forces act across the entire cross section and tend to develop a parabolic back flow, which is greatest at the center of the capillary. The capillary therefore continually tends to mix its contents, swirling the outer edges forward and the center region backward.

In the context of isotachophoresis, Everarts, Verhegen, and Van De Veene have shown by experiment that small back flows (on the order of 10%) improve the plug flow profile and sharpen the zones. See "Isotachophoretic Experiments with a Counter Flow of Electrolyte," 123 Journal of Chromatography, pp. 139–148, 1976. They stated, however, that they found that if a 100% back flow of electrolyte is applied (such that the hydrodynamic back flow of electrolyte is in equilibrium with the electrophoretic flow), the sharpness of the zone boundaries was lost. They also reported that even at 50–60% back flow of electrolyte, many zones became mixed. Of note is that these experiments were carried out using a separation capillary that had an inner diameter of 500 microns, which is ten times larger than the capillaries normally used in capillary electrophoresis.

The pressure required to induce a 10% back flow in a conventional capillary is on the order of 0.01 atmosphere, or a centimeter head of water. Although these known hydrostatic methods strive to increase resolution in different ways and under different operating conditions, they fail to deal with the problem of controlling or eliminating EOF.

Small-bore capillaries for CE are known to have the advantage that higher electric fields may be applied with less problem of developing radial temperature gradients. On the other hand, these small-bore capillaries normally suffer from greatly reduced sensitivity, since their capacity is lower and drops as the square of the capillary diameter. For example, a fifteen-micron capillary delivers less than a tenth as much sample to a detector as a fifty-micron capillary. Furthermore, detection using the smaller capillary is much more difficult, since the detection path length for UV absorbance detectors is then less than one-third as long, and the detection cell is so narrow that it is hard to focus the detection light into it without stray light worsening the desired linearity.

Another limitation of small-bore capillaries is that their few-micron double-layer region of laminar flow does not scale with size, but rather becomes a significant percentage of the total flow, thus contributing to laminar mixing and loss of resolution. For example, a 2½-micron double layer region represents less than 20% of the cross-sectional area of a fifty-micron capillary, but 75% of the area of a ten-micron capillary, thus causing very serious laminar flow and peak broadening.

SUMMARY OF THE INVENTION

A capillary electrophoresis apparatus has a capillary, through which an analyte elutes in a forward direction from an injection end to an outlet end. A conventional reservoir and injection arrangement holds the analyte and a buffer and injects the buffer and analyte into the capillary. A power supply applies an electric potential across the length of the capillary.

A back-pressure arrangement adjustably pressurizes the analyte in the capillary toward the injection end to create a backward-directed hydrostatic flow velocity component with a hydrostatic flow velocity profile that is at least 50% as strong as but oppositely directed from a forward-directed electroosmotic flow (EOF) velocity profile, thereby reducing the EOF.

The internal cross section of the capillary is preferably wider than it is high and has a height no greater than 20 microns. The capillary thereby restricts the EOF velocity profile to being substantially parabolic. The aspect ratio of the capillary is preferably at least 2:1, where the aspect ratio is a greatest interior width divided by a greatest interior height of the capillary. For most applications, the aspect ratio should be at least 5:1, and preferably 10:1 or greater. The aspect ratio chosen for any particular application will depend on the required bulk flow and manufacturing considerations. The capillary is preferably rectangular.

The invention also includes the method of applying back pressure to the analyte and of restricting the EOF velocity profile to being substantially parabolic.

DETAILED DESCRIPTION

Figure 1A:
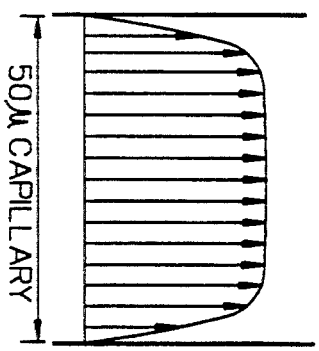
FIGS. 1a, 1b, and 1c illustrate velocity profiles of electroosmotic, composite, and hydrostatic flows, respectively, in a conventional cylindrical capillary with a fifty-micron diameter.
Figure 1B:
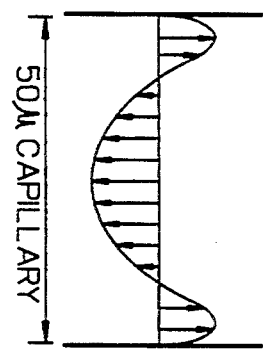
Figure 1C:
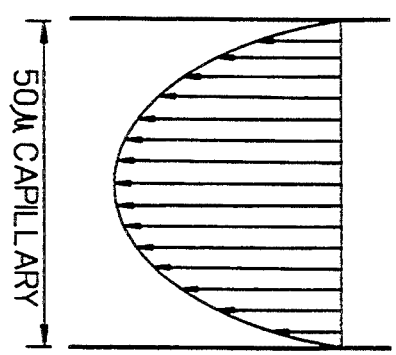

FIGS. 1a, 1b, and 1c illustrate typical velocity profiles of electroosmotic, composite, and hydrostatic flows, respectively, in a conventional cylindrical capillary with a fifty-micron diameter. The velocity profile of the forward-going EOF (FIG. 1a) is roughly planar over most of the middle region of the capillary, whereas the velocity profile of the backward-going hydrostatic flow (FIG. 1c) is parabolic. The resultant additive, composite flow has a wavy flow velocity profile, which causes undesirable eddy countercurrents, which in turn cause mixing and peak broadening.

This invention uses to advantage the phenomenon that as capillaries shrink, their EOF cross-section progressively approaches laminar flow and develops a more parabolic shape. The reason for this is that the thickness of the double layer is fairly independent of capillary diameter. The laminar flow region of the double layer therefore becomes relatively larger over the cross-section of smaller capillaries while the plug flow region in the center of the capillary shrinks. At the limit, in very tiny capillaries, the EOF becomes parabolic.

As a second step the invention creates a back flow within the capillary by applying hydrostatic back pressure end-to-end across the capillary. This flow is precisely laminar and in circular and rectangular capillaries, it develops a precisely parabolic velocity profile.

If, as is done in this invention, both the forward EOF and the back flow are induced at the same time, the net effect is determined by superposition of the two partial flows, that is, the effects of the EOF and hydrodynamic flow are added. To the extent that EOF is laminar in small capillaries, the forward-going EOF profile "parabola" and the backward-going hydrodynamic profile "parabola" cancel each other out, with the result that the EOF may be stopped, without inducing the eddy currents and mixing that would otherwise completely destroy the sharpness of the peaks.

Figure 2A:
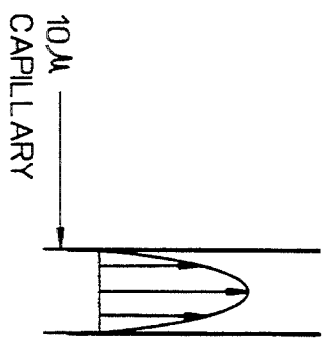
FIGS. 2a, 2b, and 2c illustrate velocity profiles of electroosmotic, composite, and hydrostatic flows, respectively, in a substantially rectangular capillary according to the invention, with an inner height of ten microns.
Figure 2B:
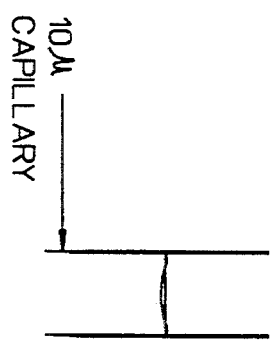
Figure 2C:
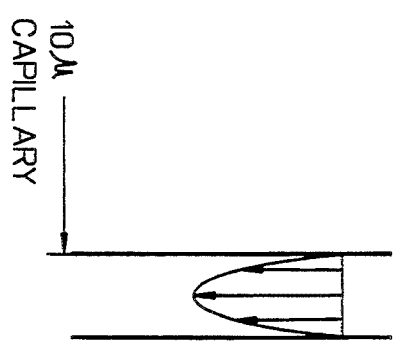

FIGS. 2a, 2b, and 2c illustrate the velocity profiles of electroosmotic, composite, and hydrostatic flows, respectively, in a capillary according to the invention, with an inner height of ten microns. As is described in greater detail below, the capillary according to the invention is preferably approximately rectangular. As FIGS. 2a, 2b, and 2c show, the approximately parabolic EOF velocity profile (FIG. 2a) is nearly exactly cancelled by the hydrostatic flow (FIG. 2c), so that the composite velocity flow profile (FIG. 2b) is flat; in other words, the flow and counterflow are essentially stopped. What little residual bending remains is negligible compared to the diffusion band-broadening that always takes place, especially in small capillaries.

Figure 3:
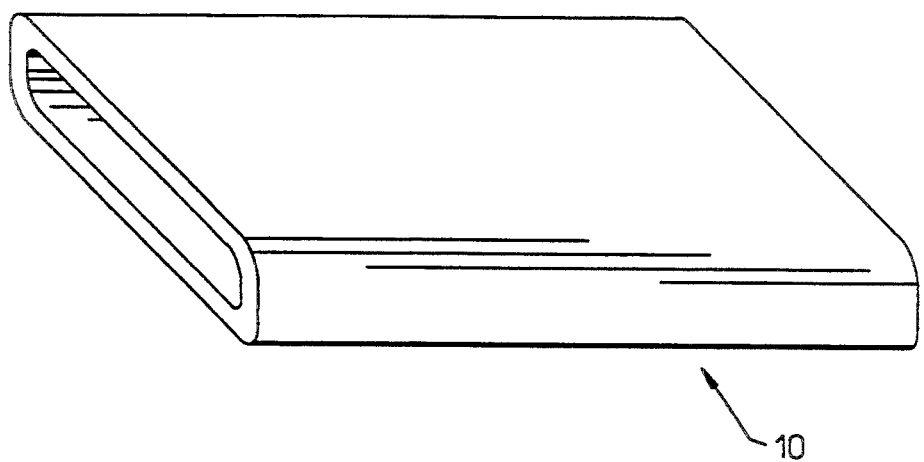
FIG. 3 is a perspective illustration of the capillary according to the invention with a rectangular cross section.

FIG. 3 illustrates the preferred general rectangular structure of a section of a capillary 10 according to the invention. In this discussion, the "width" of the capillary is its greatest internal dimension, and the "height" is the smallest internal dimension. In other words, if one were to lay the capillary on a horizontal surface and look into its end, the width is in the horizontal direction and the height is in the vertical direction. In practical embodiments of this invention, the capillary 10 is preferably high enough to allow slight residual plug flow at its center.

One advantage of such a configuration is that it maximizes sensitivity by allowing greater sample volumes to reach the detector with only a negligible reduction in resolution because of imperfect cancelling of the two flow velocity profiles. Detection becomes more difficult the smaller the capillary becomes: when the capillary diameter is on the order of only about ten microns, conventional UV detectors may lose the ability to detect altogether, in part because the absorbance path length becomes too small for efficient operation.

A wide, rectangular capillary as preferred in the invention increases the bulk flow and the absorbance path length, but its height is still kept so small that the EOF velocity profile is substantially parabolic and the thermal gradients within the capillary are greatly reduced (thus reducing the risk of convective fluid motion and allowing Stronger electric fields to be applied over the capillary).

The ratio between the cross-sectional area and the height of the capillary should therefore preferably be made as large as possible; for any given application of the invention, the maximum limit of this ratio will be determined by the manufacturing technique used to form the capillary. A minimum aspect ratio (width-to-height) of 10:1 is preferred in order to provide significant bulk flow. Tests have shown that capillaries from $5\mu \times 50\mu$ up to $15\mu \times 150\mu$ work especially well. In general, capillaries with a minimum dimension (height) of 20 microns or less are preferred for hydrostatic EOF control.

In particular, rectangular capillaries with rounded internal corners are especially well suited for use in reducing EOF: rounded corners reduce the corona that may be created at sharp corners because of the strong electric field. This is desirable since coronas change the evenness of EOF. In order to better equalize radial heat flow, the edges of the capillary (its "short sides") are preferably thicker than its wide sides in order to increase the thermal impedance in that direction.

The capillary according to the invention is preferably made by drawing down a rectangular fused silica boule to the desired size and coating it externally with polyamide.

Other advantageous capillary cross-sections include oval, elliptical, and multi-leg structures such as a star shape. As long as the aspect ratio is kept large (preferably at least 10:1), these structures maximize bulk flow while keeping at a minimum the greatest distance between any portion of the analyte and the nearest capillary wall, thereby minimizing thermal gradients and the associated convection currents.

Figure 4:
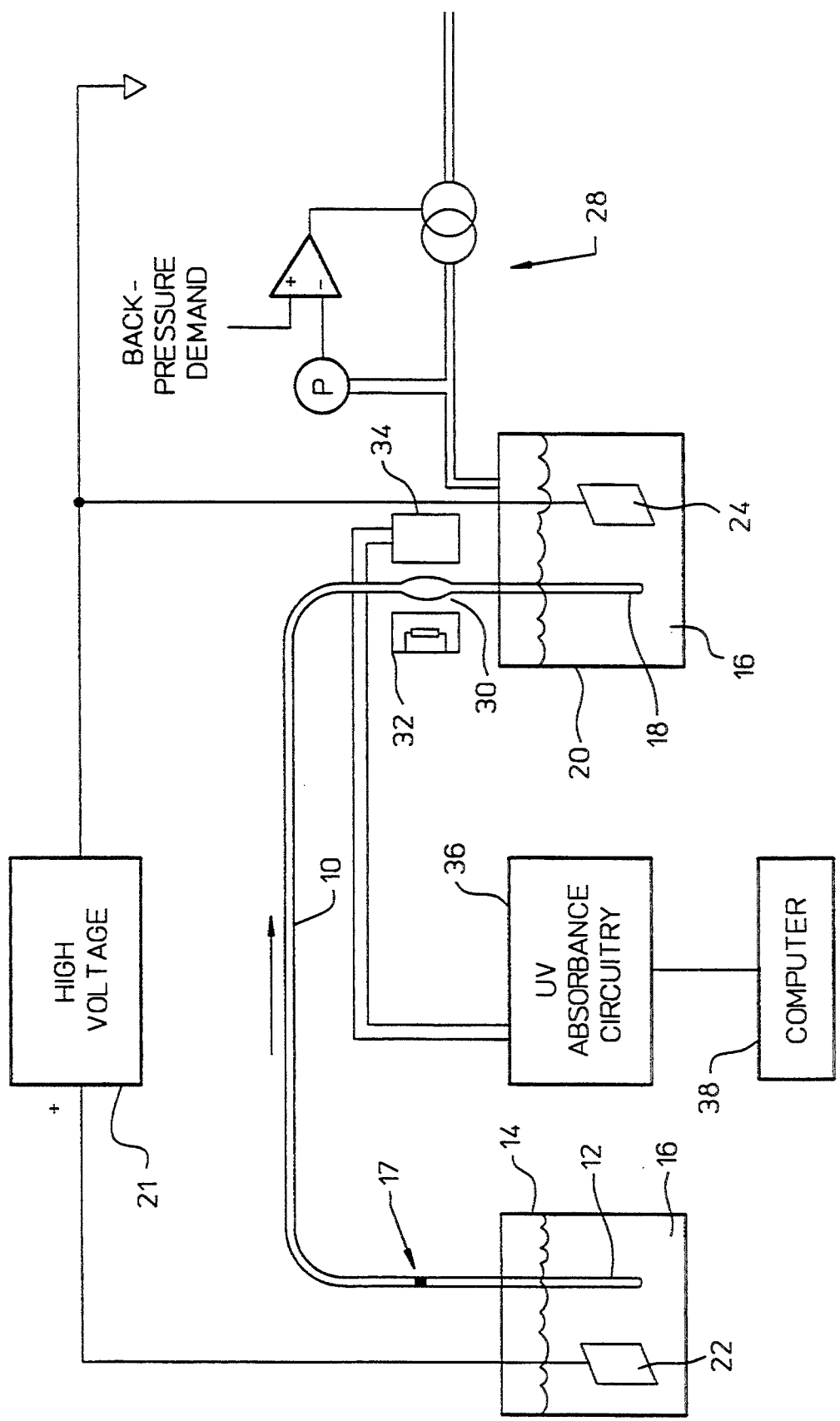
FIG. 4 is a schematic drawing of a capillary electrophoresis instrument employing the capillary and back-pressure method according to the invention.

FIG. 4 is a block diagram of a CE system. An injection end 12 of the capillary 10 extends into or is connected with an injection or inlet reservoir 14 (such as a vial) that holds a buffer 16. Separate reservoirs for the analyte and buffer will normally be provided: buffer is first injected into the capillary, followed by an amount of the analyte, followed by more buffer; this technique is well known. In FIG. 4, a "plug" of analyte 17 is shown near the injection end within the capillary, before analyte has begun to separate into bands. The capillary 10 preferably has the rectangular shape shown in FIG. 3. The analyte 17 is injected using known equipment into the injection end 12 and, as it migrates through the capillary, its components separate into bands. The analyte exits the capillary at an output end 18 and is voided into a waste or outlet reservoir 20.

A source 21 of high voltage, which may be a conventional 30 kV power supply, applies the strong electric field over the capillary 10 via anode and cathode electrodes 22, 24, which are electrically connected to the buffer solution in the inlet and outlet reservoirs 14, 20, respectively. Backward hydrostatic or hydrodynamic pressure, that is, pressure tending to push the analyte back in the direction of the injection end 12 of the capillary 10, can be applied to the buffer using a regulated pressure pump 28, which may, for example, pressurize the outlet reservoir 20.

The pump 28 may be of any conventional type, such as a pressure-servo diaphragm pumps. The back pressure set point and regulation or demand signal that are used to control the pressure of the pump 28 may be stored in or generated by conventional control circuitry (not shown) such as a microcomputer with suitable known user input devices. The actual servo control of the pump may be accomplished in any known manner. Typically, the servo system will include a pressure sensor whose output is fed back to the control circuitry and compared with the setpoint pressure. The difference between actual and setpoint pressure is then amplified and used to control pump speed. The pressure sensor, feed-back and differencing circuitry, amplifier and other regulation devices are well understood in the field of automatic control and are therefore not shown or described further.

As the analyte 17 moves forward through the capillary 10, its separated component bands pass through a detector, which includes a detection region 30 of the capillary, a light source 32, and a sensor 34. Light energy (typically UV light) is focussed from the light source 32 to pass through the analyte 17 in the detection region 30, and is sensed by the conventional sensor 34. The sensor 34 is electrically connected to conventional absorbance circuitry 36, which determines the instantaneous light absorbance of the analyte in the detection region. The absorbance circuitry 36 is electrically connected to standard processing circuitry, such as a computer 38, which determines whether a peak is present in the detection region, its width, the time of its passage through the capillary, and other well-known factors used to identify species in a CE analyte. The factors and required calculations are well known in the art; this invention makes it possible to have more sharply defined peaks by controlling EOF. The computer 38 may also be used as the control circuitry for controlling the pump 28.

According to the invention, differential pressure is applied end-to-end across the separation capillary. In particular, the back pressure pump 28 applies a positive pressure to the output end 18 of the capillary to create the parabolic hydrostatic flow profile shown in FIG. 2c. The back pressure required in any given application depends on various factors such as the exact dimensions of the capillary and the magnitude of the separations potential applied. Unlike the mild pressures used in the prior art to flatten the plug flow fronts, however, the back pressure used to control EOF in the invention is considerably greater and runs from one tenth to hundreds of atmospheres.

Pressure is often otherwise applied before a run for the purpose of etching, coating, or otherwise chemically conditioning a capillary before a run. The user may determine the proper differential pressure during such steps, and will often be able to use the same equipment. According to this invention, however, back pressure that is much higher than that used in conventional systems is applied to the capillary during the actual operation of the instrument, that is, when the high separation voltage is applied.

In one prototype of the invention, the conventional, round, 50μ separation capillary was replaced with a 10μ×100μ rectangular capillary. The length of the capillary was 25 cm, roughly half the length conventionally used, which provided twice the axial field strength. Normally, with such a configuration, the separation time would drop by a factor of four, for example from 4 minutes to 1 minute: this is the time it takes EOF to transport the electrolyte and any uncharged constituents in the sample from the injection end of the capillary to the detection region.

Instead of venting the waste vial to atmospheric pressure (the conventional procedure), back pressure was additionally applied to the outlet or waste vial 20. This pressure induced a back flow of electrolyte, which "flattened" the forward EOF and thus stopped greatly retarded the undesirable forward EOF.

Several methods may be used to determine how much back pressure is needed to stop the EOF. For any implementation of the invention, simple experimentation using trial runs of the buffer and the analyte at various differential pressures, followed by analysis of the resulting peaks, will show the user which differential pressure needs to be applied to create the sharp, "cancelled-parabolic" composite flow illustrated in FIG. 2b. One method is to adjust the back pressure until identifiable peaks move backwards and forwards past the detector.

Another approximate method for small capillaries is to compute the EOF pressure. To do this, the EOF velocity must first be measured, for example by timing a run without any applied pressures. For circular capillaries, the pressure formula is as follows:

$$P = \frac{8 \cdot v \cdot L \cdot F}{\pi \cdot R^4}$$

where
P=pressure;
$v$=fluid viscosity;
L=capillary length;
F=flow rate; and
R=capillary radius.

For example, a 10 micron circular capillary 25 mm long, carrying an electrolyte with the same viscosity as water, at a velocity of 1 mm/sec, requires a back pressure of 20 atmospheres. The pressure calculation for rectangular capillaries such as the capillary according to this invention is more complicated since it involves hyperbolic functions, but well-known numerical techniques may be used to perform these calculations if the greater accuracy is required. In general, however, for capillaries of comparable width, however, rectangular capillaries require similar but somewhat lower pressures than do round ones.

Yet another way to derive the EOF pressure (against which the equivalent back pressure is applied) is to compare the retention times for a known back pressure to those with no pressure. For example, if 5 atmospheres are observed to cut the velocity in half (retention times doubled), then 10 atmospheres can be expected to stop the flow entirely.

As FIGS. 2a-2c illustrate, one can stop EOF using the invention by applying a back pressure that has a flow velocity profile that is substantially equal but opposite to the velocity profile of the EOF. On the other hand, the ability to stop EOF also provides the ability to control it: by applying less than equal back pressure, one may control how much the flow velocity profile "bulges," that is, how flat the EOF profile is allowed to be.

Once the EOF pressure is known or estimated, several measurement strategies are possible. A preferred strategy is to run the experiment with constant yet incomplete EOF cancellation, such that the constituents eventually elute without further intervention. For example, the apparatus might be run at 75% EOF cancellation, such that the run takes four times as long as without back pressure. This strategy has the advantage that peaks move through the detector more slowly; low-pass filtering can then be used to improve the signal-to-noise ratio. With four times the retention time, the resolution would equal that of a separation performed at four times the voltage.

This invention works particularly well when the detection region 30 (FIG. 4) is formed as a bubble-shaped section of the capillary 10. Such a "bubble cell" section is disclosed in U.S. Pat. No. 5,061,361 (Gordon, 29 Oct. 1991). Since the EOF may be controlled using the invention, an experiment may be run much longer without premature eluting of the separated constituents of the sample. In other words, several difficult-to-separate peaks of an analyte may be split by prolonging their time in the CE apparatus.

Figure 5:
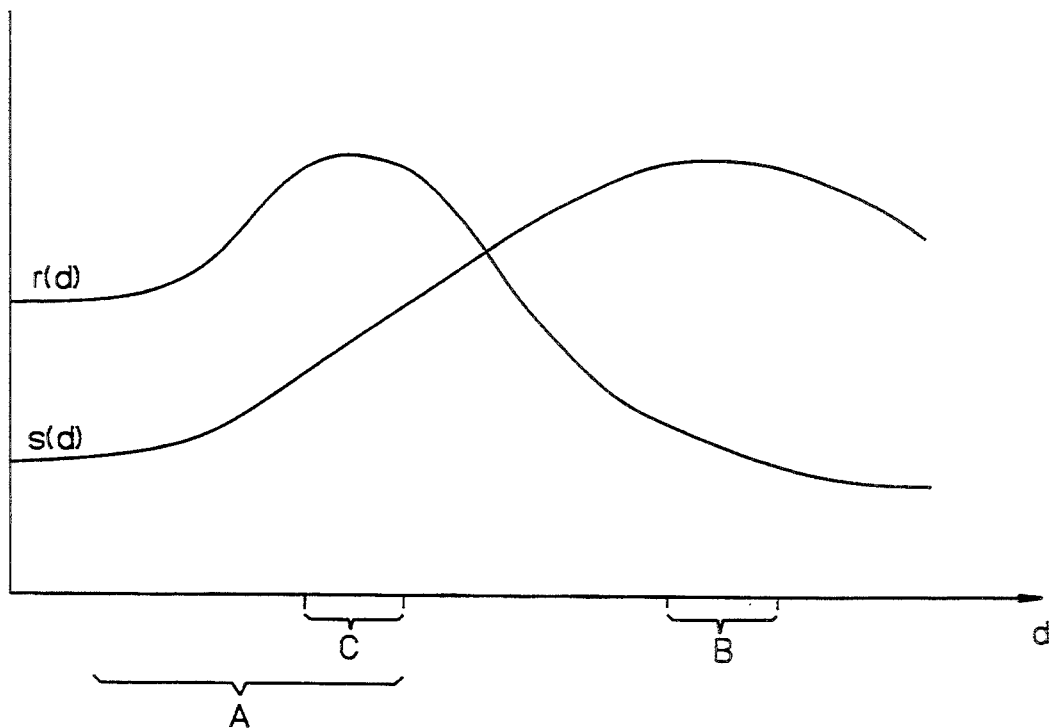
FIG. 5 is a qualitative illustration of the way in which CE resolution and sensitivity vary as functions of the inner diameter of the separation capillary under the influence of back pressure according to the invention.

FIG. 5 is a qualitative illustration of the way in which CE resolution r(d) and sensitivity s(d) vary as functions of the inner diameter d of the separation capillary. The operating region for a small-bore capillary with back pressure according to the invention (as in FIG. 2) is shown as region A. The operating region for a standard unpressurized capillary is shown as region B. As FIG. 5 illustrates, the capillary according to the invention has much better resolution, albeit at the cost of lessened sensitivity.

When back pressure is applied, the resolution curve r(d) will display a "hump" over a range C of diameters. The range can be changed by changing the amount of back pressure. The diameter range C also determines the preferred operating region of the invention. By allowing a slight plug flow (less than 100% EOF cancellation), the analyte may elute with minimal hydrostatic degradation, that is, without too much mixing. In order to maintain sufficient EOF control, however, the backward-directed hydrostatic flow velocity profile should be at least 50% of (but oppositely directed from) the forward-directed velocity profile of the EOF.

The invention overcomes many problems that plague conventional, round CE capillaries. The invention takes advantage of the capacity of small-bore capillaries for higher fields, which provides faster separations. By providing a rectangular capillary with a high aspect ratio, the invention also avoids the loss of sensitivity that is normally encountered when using small capillaries.

By overcoming EOF, the invention also greatly increases resolution without requiring extraordinarily high-voltage power supplies by prolonging the separation time. As an illustration, for a given power supply, if the separation time is quadrupled, the separation in time between two peaks would also quadruple. Even though their widths would double due to diffusion, there would still be a net gain of two in the ability to resolve the two peaks. This gain is readily achieved using this invention. Achieving it using conventional methods, however, would require both quadrupling the length of the separations capillary and also quadrupling the applied separation voltage. To achieve separation equal to that of the invention, sophisticated, laboratory-grade 120 kV power supplies would be required instead of a common 30 kV supply, which is even found in many television sets.

The invention is thus faster, more sensitive, more economical, and has better resolution than conventional CE systems that do not address the problem of EOF.

I claim:

1. A capillary electrophoresis method comprising the following steps:

A. injecting an analyte and buffer into an injection end of a capillary to permit the analyte and buffer to elute in a forward direction toward an outlet end of the capillary;

B. applying an electric potential across the length of the capillary between the injection end and the outlet end;

C. adjustably pressurizing the analyte in the capillary toward the injection end with a backward-directed hydrostatic flow velocity component with a hydrostatic flow velocity profile that is at least 50% as strong as but oppositely directed from a forward-directed electroosmotic flow (EOF) velocity profile, whereby the EOF is reduced; and D. restricting the EOF velocity profile to a substantially parabolic profile.

2. A capillary electrophoresis apparatus comprising:

A. a capillary that has an injection end, through which an analyte enters the capillary, and an outlet end, toward which components of the analyte migrate and separate in a forward direction, said capillary having an internal cross section that includes at least a first, greater internal dimension which is defined as the capillary width and a second, smaller internal dimension which is defined as the capillary height, wherein the Capillary height is no greater than 20 microns, and wherein the height and width of the capillary define a capillary aspect ratio that is a function of the greatest interior width of the capillary divided by the greatest interior height of the capillary;

B. reservoir and injection means for holding the analyte and a buffer and for injecting the analyte into the injection end of the capillary;

C. voltage means for applying an electric potential across the length of the capillary between the injection end and the outlet end; and D. controllable back pressure means for pressurizing the analyte in the capillary toward the injection end, for creating an adjustable backward-directed hydrostatic flow velocity component with a hydrostatic flow velocity profile that is at least 50% as strong as but oppositely directed from a forward-directed electroosmotic flow (EOF) velocity profile, and for thereby reducing the EOF;

whereby said capillary provides an EOF conditioning means that restricts the EOF velocity profile to a substantially parabolic profile.

3. An apparatus as defined in claim 1, in which the aspect ratio of the capillary is at least 5:1.

4. An apparatus as defined in claim 3, in which the capillary is rectangular.

* * * * *